United States Patent
Laskin et al.

(10) Patent No.: US 9,290,484 B2
(45) Date of Patent: Mar. 22, 2016

(54) FURYL AND THIENYL TRIAZOLE DERIVATIVES AND THERAPEUTIC USES THEREOF

(71) Applicant: University of Medicine and Dentistry of New Jersey, Somerset, NJ (US)

(72) Inventors: Jeffrey D. Laskin, Piscataway, NJ (US); Diane E. Heck, Rumson, NJ (US); Geraldine Guillon, Macungie, PA (US); Thomas Finetti, Livingston, NJ (US); Angela Hunter, Mickleton, NJ (US); Christophe Guillon, Macungie, PA (US); Robert D. Rapp, Laurel Dale, PA (US); Anna M. Vetrano, Hamilton, NJ (US); Ned D. Heindel, Easton, PA (US)

(73) Assignees: RUTGERS, THE STATE UNIVERSITY OF NEW JERSEY, New Brunswick, NJ (US); LEHIGH UNIVERSITY, Bethlehem, PA (US)

( * ) Notice: Subject to any disclaimer, the term of this patent is extended or adjusted under 35 U.S.C. 154(b) by 67 days.

(21) Appl. No.: 13/774,231

(22) Filed: Feb. 22, 2013

(65) Prior Publication Data

US 2014/0243381 A1     Aug. 28, 2014

(51) Int. Cl.
| | |
|---|---|
| C07D 249/14 | (2006.01) |
| C07D 249/12 | (2006.01) |
| A61K 31/42 | (2006.01) |
| C07D 409/04 | (2006.01) |
| C07D 405/04 | (2006.01) |
| C07D 405/14 | (2006.01) |
| C07D 409/12 | (2006.01) |
| C07D 409/14 | (2006.01) |
| A61K 31/4196 | (2006.01) |

(52) U.S. Cl.
CPC ............ *C07D 409/04* (2013.01); *C07D 405/04* (2013.01); *C07D 405/14* (2013.01); *C07D 409/12* (2013.01); *C07D 409/14* (2013.01); *A61K 31/4196* (2013.01)

(58) Field of Classification Search
CPC .. C07D 249/12; C07D 405/14; C07D 409/14; C07D 409/12; A61K 31/4196

USPC ................ 548/263.8, 263.2, 264.2; 514/380
See application file for complete search history.

(56) References Cited

U.S. PATENT DOCUMENTS

| | | | |
|---|---|---|---|
| 6,586,453 B2* | 7/2003 | Dhanoa et al. ............... 514/365 |
| 2003/0125562 A1* | 7/2003 | Heindel et al. ............ 546/272.4 |

OTHER PUBLICATIONS

Patani et al. "Bioisosterism: A rational approach in drug design," Chem. Rev. 1996, vol. 96, pp. 3147-3176.*
Kusebauch et al. "Assesing oxazole bioisosteres as mustasynthons on Rhizoxin assembly line," ChemBioChem, 2011, vol. 12, No. 15, pp. 2284-2286.*
Hou et al. "Synthesis and bacteriostatic activity of new thiosemicarbazone derivatives—amino mercaptotriazole Schiff bases," Yaoxue Xuebao, 1992, vol. 27, No. 10, pp. 738-742.*

* cited by examiner

*Primary Examiner* — Shengjun Wang
(74) *Attorney, Agent, or Firm* — Fox Rothschild LLP (57) ABSTRACT

Nitric oxide biosynthesis-inhibiting anti-inflammatory and anti-microbial compounds of Formula (3) and Formula (4) wherein R1 and R2 are independently selected from optionally substituted thienyl, optionally substituted furyl, optionally substituted —CH═CH-thienyl and optionally substituted —CH═CH-furyl, provided that R2 is substituted with as nitro group

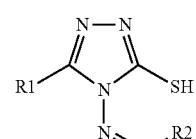

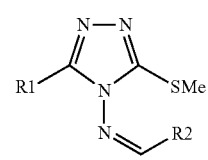

Treatment methods utilizing the compounds, and methods of synthesis of the compounds are also disclosed.

3 Claims, 2 Drawing Sheets

Figure 1: Nitrofuran-containing antibacterials

Nitrofurantoin

Nitrofurazone

Figure 2: Inhibition of Induced Nitric Oxide Biosynthesis by Compound 3i

FURYL AND THIENYL TRIAZOLE DERIVATIVES AND THERAPEUTIC USES THEREOF

FIELD OF THE INVENTION

The invention is directed to as unique class of thienyl and furyl imines of 4-amino-1,2,4-triazoles, having utility as antinitric oxide and antibacterial therapeutic agents.

BACKGROUND OF THE INVENTION

The 1,2,4-triazole nucleus is an important pharmacophore found in antifungal, antitubercular, antiparasitic, antileukemic, and antitumor therapeutic agents. Certain 1,2,4-triazoles have a direct action on leukemia. Certain 1,2,4-triazoles also serve as therapeutic adjuvants by suppressing azole-resistant fungal infections associated with cancer chemotherapy. Several N-substituted 1,2,4-triazoles, including anastrozole, letrozole, and vorozole, act as aromatase inhibitors, and show impressive activity in the treatment of advanced breast cancer. These established antitumor triazoles are useful as templates for new generations of candidate chemotherapeutics for estrogen- and androgen-dependent diseases, based on 1,2,4-triazoles.

Figure 1:
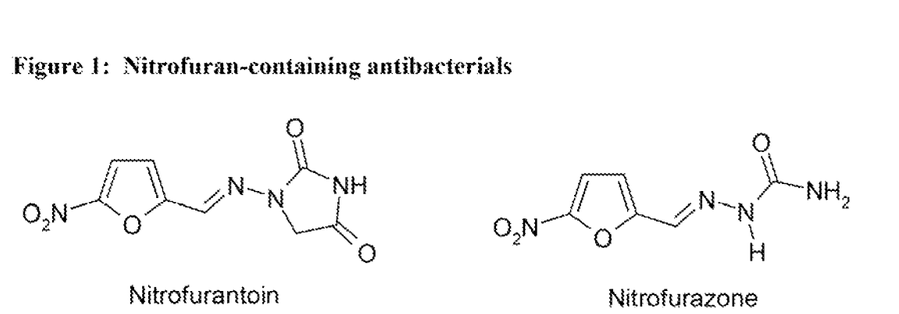
FIG. 1 displays the chemical structures of the known nitrofuran antibiotics Nitrofuratoin and Nitrofurazone.

5-Nitrofuran derivatives were the first commercially known nitrogenous heterocycles of medicinal value, primarily because of their effectiveness against both Gram positive and Gram negative bacteria. However, their use in treating human infections has always been highly problematic. Over 4,000 nitrofuran-based therapeutic compounds have been synthesized and tested for their biological effectiveness to date, despite the fact that the nitro functional group has been reported to be carcinogenic, and to cause methemoglobinemia. Sustained oral administration (although not long-term topical application) has been associated with hepatic and pulmonary toxicities. Some of the more commonly known 5-nitrofuran-based therapeutics include nitrofurantoin and nitrofurazone (FIG. 1), both of which are widely utilized as antibacterial, agents.

BRIEF SUMMARY OF THE INVENTION

One aspect of the present invention is directed to a method of treating an infection in a human or an animal, comprising administering a therapeutically effective amount of at least one compound of Formula (3) or Formula (4), where R1 and/or R2 are independently selected from the group consisting of optionally substituted thienyl, optionally substituted furyl, optionally substituted aryl, optionally substituted —CH=CH-thienyl, optionally substituted —CH=CH-furyl and optionally substituted —CH=CH-aryl, provided that at least one of R1 and R2 is optionally substituted thienyl, optionally substituted furyl, optionally substituted —CH=CH-thienyl, or optionally substituted —CH=CH-furyl Preferably R1 and/or R2 are selected from the group consisting of optionally substituted thienyl, optionally substituted furyl, optionally substituted —CH=CH-thienyl and optionally substituted —CH=CH-furyl. Preferably at least one of R1 and R2 is substituted with a nitro group. More preferably, R2 is substituted with a nitro group.

The compounds of Formula (3) and Formula (4) possess antibiotic activity, preferably antibacterial activity. Preferably the compounds are active against bacterial vaginosis. Preferably, the compounds of Formula (3) and Formula (4) are also nitric oxide synthase inhibitors, and possess anti-inflammatory activity. Most preferably, the compounds of Formula (3) and Formula (4) possess both antibacterial activity and anti-inflammatory activity in the same molecule.

In a preferred method of the invention, the infection is due to a microorganism selected from the group consisting of gram negative, gram positive and gram-variable microorganisms. Preferably, the gram negative microorganism is *Escherichia coli*. Preferably, the gram positive microorganism is *Staphylococcus aureus*. Preferably the gram-variable microorganism is *Gardnerella vaginalis*. Preferably the microorganism is controlled by the treatment. Most preferably, the microorganism is killed or eliminated by the treatment. Preferably the treatment is by topical administration, where at least one compound of Formula (3) or Formula (4) is applied as a topical formulation comprising at least one pharmaceutically acceptable adjuvant adapted for topical treatment.

Another aspect of the invention is directed to a method of treating inflammation, comprising administering a therapeutically effective amount of at least one compound of Formula (3) or Formula (4), where R1 and/or R2 are independently selected from the group consisting of optionally substituted thienyl, optionally substituted furyl optionally substituted aryl, optionally substituted —CH=CH-thienyl, optionally substituted —CH=CH-furyl and optionally substituted —CH=CH-aryl, provided that at least one of R1 and R2 is optionally substituted thienyl, optionally substituted furyl, optionally substituted —CH=CH-thienyl, or optionally substituted —CH=CH-furyl. Preferably, the optionally substituted thienyl, optionally substituted furyl, optionally substituted —CH=CH-thienyl, or optionally substituted —CH=CH-furyl is substituted with a nitro group. Preferably the inflammation is associated with bacterial vaginosis, and treatment comprises topical application of a topical formulation comprising at least one pharmaceutically acceptable adjuvant adapted for topical treatment.

Yet another aspect of the invention is directed to a compound of Formula (3) or Formula (4) wherein R1 and R2 are independently selected from the group consisting of optionally substituted thienyl, optionally substituted furyl, optionally substituted —CH=CH-thienyl, and optionally substituted —CH=CH-furyl, provided that R2 is substituted with a nitro group. Preferably, the compound possesses antibiotic activity, more preferably antibacterial activity, and most preferably antibacterial activity against at least one pathogen associated with bacterial vaginosis. Preferably, the compound inhibits nitric oxide synthesis. Preferably, the compound possesses anti-inflammatory activity. Most preferably, the compound possesses both antibacterial activity and anti-inflammatory activity.

Still another aspect of the invention is directed to a pharmaceutical composition comprising at least one compound of Formula (3) or Formula (4), and at least one compound selected from the group of pharmaceutically acceptable adjuvants, carriers, diluents and excipients. A related aspect of the invention is directed to a topical pharmaceutical composition wherein the compound selected from the group of pharmaceutically acceptable adjuvants, carriers, diluents and excipients is selected for topical use.

DETAILED DESCRIPTION OF PREFERRED EMBODIMENTS

The compounds of the present invention contain two —N=N— (azo imine) functional groups and at least two five-membered heterocyclic rings. In contrast, both nitrofurantoin and nitrofurazone contain a single azo imine functional group, and nitrofurazone contains only one 5-membered heterocyclic ring. However, the presently claimed compounds, viz. 3 and 4, do not contain (1) the aza-urea moiety [=N—NH—CO—NH—], also known as a semicarbazone, nor (2) the hydrogen bonding but labile amidic N—H moiety of the existing nitrofuryl antibacterials, as exemplified by nitrofurantoin and nitrofurazone. Surprisingly, even with these structural differences versus prior art compounds, the profile of antibacterial activity for compounds of the invention (see Table 1) is equal to or greater than that of nitrofurantoin against the vaginotropic pathogen. Gardnerella vaginalis, which often causes bacterial vaginosis by a recto-vaginal pathway. The other common vaginal bacterial vector, E. coli, is also controlled by compounds of the present invention.

At the same time many of the compounds of the classes claimed herein display potent anti-inflammatory activity as evidenced by inhibition of cytokine-induced nitric oxide synthase. Since bacterial vaginosis and inflammatory vaginitis frequently co-exist, the use of agents able to address both conditions simultaneously in a single compound offers as therapeutic advantage. It is well known that nitric oxide regulates a great many physiological and pathological processes in vivo, including inflammation, growth control, vascular tone, muscle contraction, nerve transmission, among others. Control of nitric oxide in vivo is mediated by different enzymes including inducible nitric oxide synthase, endothelial nitric oxide synthase and brain nitric oxide synthase. Compounds of the present invention are effective inhibitors of inducible nitric oxide synthase, and may also inhibit other forms of the enzyme, and thereby regulate nitric oxide functioning throughout the body.

The claimed compounds can be prepared by either of two alternative pathways as indicated below. The platform pharmacophore intermediate 2 can be prepared using one of at least two different synthesis pathways (Scheme 1).

When intermediates 2 are condensed with an aldehyde (Scheme 2), they are converted in >80% yields to compounds of Class 3, and subsequently by alkylation, preferably methylation, to compounds of Class 4. When a specific member of either Class 3 or 4 possesses an optionally substituted aryl group or an optionally substituted heterocycle, preferably an optionally substituted five-membered heterocycle, at locus R1, together with a specific imine-like side chain terminating in an optionally substituted aryl group or an optionally substituted heterocycle, preferably an optionally substituted live-membered heterocycle, more preferably a heterocycle identical to or similar to that of R1, and further containing as nitro group at locus R2, then this hitherto undisclosed class of compounds displays useful activity against Gardnerella vaginalis, S. aureus and E. coli, as well as useful activity as a nitric oxide synthase inhibitor.

For the purposes of the present invention, the term "similar" with regard to two different heterocycles is taken to mean having the same ring size (e.g., 5- or 6-membered rings), and differing only in the degree of unsaturation within the ring (e.g., fully aromatic or partially reduced), and/or differing in the number and type of heteroatoms one S versus one O; or one S versus S and N). Preferably, the similar heterocyclic rings are selected from the group consisting of thiophene, furan, pyrrole, pyrazole, imidazole, oxazole, isoxazole, thiazole and isothiazole. Most preferably, the similar heterocyclic rings are selected from the group consisting of thiophene and furan. In addition, nitric oxide synthase inhibitory activity is also observed in compounds of classes 3 and 4 which lack the five-membered nitro-containing ring at R2 (see examples 3h, 3i, 4i, 3j, and 4j, Table 1).

The specific and unique utility for the identified group of synthetic aldimine derivatives of 2, namely, compounds of types 3 and 4, is the ability to treat bacterial infections, with the concomitant inhibition of nitric oxide biosynthesis thereby providing simultaneous anti-inflammatory activity.

Structure-activity studies (see biological data in Table 1) reveal that converting a member of the 3 series to its counterpart in the 4 series by alkylation (e.g., by methylation), increases nitric oxide synthase inhibitory activity. A nitro group on a furyl or thienyl R2 ring is necessary for high antibacterial activity, but not for NOS inhibition; however, it is clear that these effects can co-exist because compound 3e is both an antibacterial agent and a potent inhibitor of nitric oxide synthase. Further, the nitrothiophenes were observed to be more potent antibacterials against *G. vaginalis* than the nitrofurans.

The substituent at R2 can be a vinylogue (i.e., a substituent connected via a —CH═CH— linking group), as exemplified by compound 3c. In fact, R2 cinnamyl moieties (phenyl-CH═CH—), with or without nitro groups on the phenyl ring, constitute excellent nitric oxide synthase inhibitors; however, even within this chummy subset, the best NOS inhibitor, compound 4a, also contains a nitro group.

One aspect of the present invention is directed to a method of treating an infection in a human or an animal, comprising administering a therapeutically effective amount of at least one compound of Formula (3) or Formula (4), or one of the optical or geometrical isomers thereof, or one of the salts or other derivatives thereof, where R1 and/or R2 are independently selected from the group consisting of optionally substituted thienyl, optionally substituted furyl, optionally substituted aryl, optionally substituted —CH═CH-thienyl, optionally substituted —CH═CH-furyl and optionally substituted —CH═CH-aryl, provided that at least one of R1 and R2 is optionally substituted thienyl, optionally substituted furyl, optionally substituted —CH═CH-thienyl, or optionally substituted —CH═CH-furyl Preferably R1 and/or R2 are selected from the group consisting of optionally substituted thienyl, optionally substituted furyl, optionally substituted —CH═CH-thienyl and optionally substituted —CH═CH-furyl. Preferably at least one of R1 and R2 is substituted with a nitro group. More preferably, R2 is substituted with a nitro group.

As used herein, the term "therapeutically effective amount" means that amount of a drug or pharmaceutical agent, or that amount of to combination of drugs or pharmaceutical agents that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder, as was known in the art as of the date of the present invention.

Methods of treatment are disclosed herein, comprising administering therapeutically effective amounts of the inventive compounds or compositions. As used herein, the mode of "administration" or "administering" can include any commonly known clinical or medical mode, including without limitation, oral, intravenous, intramuscular and topical. A preferred mode of administration is topical application. The compositions for topical application contain at least one compound of Formula (3) or Formula (4) as defined above, or one of the optical or geometrical isomers thereof, or one of the salts or other derivatives thereof, at a concentration preferably ranging from about 0.001% to about 5% by weight relative to the total weight of the topical composition. In one preferred embodiment, the topical composition contains a compound of Formula (3) or Formula (4), or one of the optical or geometrical isomers thereof, or one of the salts or other derivatives thereof, in about 1% by weight.

The term "aryl" as used in the present application denotes monocyclic or polycyclic unsaturated hydrocarbon systems characterized by aromaticity. Such aromatic groups include phenyl, naphthyl, and the like. The term "alkyl" denotes aliphatic hydrocarbon residues of 1 to about 20 carbon atoms, preferably lower alkyl of 1 to about 6 carbon atoms. Where possible, alkyl groups may be linear, branched or cyclic. Preferred alkyl groups include, without limitation, methyl, ethyl, and linear, branched or cyclic $C_3$ to $C_6$ moieties. Most preferred is methyl. The term "heteroaryl" denotes aromatic hydrocarbon systems containing at least one N, S or O atom. Heteroaryl groups include, without limitation, pyridyl, pyrrolyl, furyl, thienyl, oxazolyl, thiazolyl, imidazolyl, and pyrazolyl.

With reference to the S-alkylation of compounds of formula (3) to form compounds of formula (4), the S—R groups include lower alkyl groups as defined above, as well, as benzyl, lower haloalkyl, lower hydroxyalkyl and lower alkoxyalkyl.

The optional substituents, when present, include halogen, nitro, cyano, COOH, COOR, CONH$_2$, CONHR, CONR$_2$, aryl, heteroaryl, benzyl, alkyl, arylalkyl, heteroarylalkyl, haloalkyl, hydroxyalkyl, alkoxyalkyl, alkoxy, haloalkoxy, thioalkoxy, and halothioalkoxy, wherein R is lower alkyl, from which the optional substituents are independently selected.

The compounds of Formula (3) and Formula (4) possess antibiotic activity against various microorganisms, preferably antibacterial activity. Preferably the compounds are active against bacterial vaginosis. Preferably, the compounds of Formula (3) and Formula (4) are also nitric oxide synthase inhibitors, and possess anti-inflammatory activity. Most preferably, the compounds of Formula (3) and Formula (4) possess both antibacterial activity and anti-inflammatory activity in the same molecule.

In a preferred method of treatment, the treated infection is due to a microorganism selected from the group consisting of gram negative, gram positive and gram-variable microorganisms. Preferably, the gram negative microorganism is *Escherichia coil*. Preferably, the gram positive microorganism is *Staphylococcus aureus*. Preferably the gram-variable microorganism is *Gardnerella vaginalis*. Preferably the microorganism is controlled by a therapeutically effective amount of the inventive compound. Most preferably, the microorganism is killed or eliminated by the treatment. Preferably the treatment is by topical administration, where at least one compound of Formula (3) or Formula (4), or one of the optical or geometrical isomers thereof, or one of the salts or other derivatives thereof, is applied as a topical formulation comprising at least one pharmaceutically acceptable adjuvant adapted for topical treatment.

Another aspect of the invention is directed to a method of treating inflammation, comprising administering a therapeutically effective amount of at least one compound of Formula (3) or Formula (4), or one of the optical or geometrical isomers thereof, or one of the salts or other derivatives thereof, where R1 and/or R2 are independently selected from the group consisting of optionally substituted thienyl, optionally substituted furyl, optionally substituted aryl, optionally substituted —CH=CH-thienyl, optionally substituted —CH=CH-furyl and optionally substituted —CH=CH-aryl, provided that at least one of R1 and R2 is optionally substituted thienyl, optionally substituted furyl, optionally substituted —CH=CH-thienyl, or optionally substituted —CH=CH-furyl. Preferably, the optionally substituted thienyl, optionally substituted furyl, optionally substituted —CH=CH-thienyl, or optionally substituted —CH=CH-furyl comprises a nitro group. Preferably the inflammation is associated with bacterial vaginosis, and treatment comprises topical application of a topical formulation comprising at least one compound of formula (3) or formula (4), or one of the optical or geometrical isomers thereof, or one of the salts or other derivatives thereof, and at least one pharmaceutically acceptable adjuvant adapted fir topical treatment.

Yet another aspect of the invention is directed to a compound of Formula (3) or Formula (4), or one of the optical or geometrical isomers thereof, or one of the salts or other derivatives thereof, wherein R1 and R2 are independently selected from the group consisting of optionally substituted thienyl, optionally substituted furyl, optionally substituted —CH=CH-thienyl, and optionally substituted —CH=CH-furyl, provided that R2 is substituted with a nitro group. Preferably, R1 and R2 are independently selected from optionally substituted thienyl and optionally substituted furyl, provided that R2 is substituted with a nitro group. Preferably, the compound possesses antibiotic activity, more preferably antibacterial activity, and most preferably antibacterial activity against at least one pathogen associated with bacterial vaginosis. Preferably, the compound inhibits nitric oxide synthesis. Preferably, the compound possesses anti-inflammatory activity. Most preferably, the compound possesses both antibacterial activity and anti-inflammatory activity in the same molecule.

Still another aspect of the invention is directed to as pharmaceutical composition comprising at least one compound of Formula (3) or Formula (4), or one of the optical or geometrical isomers thereof, or one of the salts or other derivatives thereof, and at least one compound selected from the group of pharmaceutically acceptable adjuvants, carriers, diluents and excipients. A related aspect of the invention is directed to a topical pharmaceutical composition wherein the compound selected from the group of pharmaceutically acceptable adjuvants, carriers, diluents and excipients is selected for topical use.

EXAMPLES

Materials and Methods

Unless otherwise indicated, all materials were purchased from commercial suppliers and used without further purification. Compound 2 (R1=2-thienyl) was prepared as described by Reid, et al. (Reid J R and Heindel N D; Improved Syntheses of 5-Substituted-4-amino-3-mercapto-(4H)-1,2,4-triazoles, *J. Heterocyclic Chem.*, 1976, 13(4), 925-6; incorporated herein by reference) and compound 2 (R1=4-hydroxyphenyl) was prepared as described by Kurzer, et al. (Kurzer F, Wilkinson M, Hydrazinolysis of 3-benzoyldithiocarbazic acid esters. A correction of the literature, *J. Chem. Soc.*, (C). 1969, 1218; incorporated herein by reference). Compound 2 (R1=2-furyl) was prepared from 2-furylcarboxylic acid hydrazide by the general method of Reid, et al., in 71% yield (recrystallized from ethanol). Melting points of the two known N-aminotriazoles matched those reported in the literature, the m.p. of compound 2 (R1=2-furyl) was 210-211° C. and combustion analyses for C, H, N were within 0.4% of theoretical values.

IR spectra were recorded using a Mattson Polaris FT-IR spectrophotometer. Solids compounds were analyzed using the KBr disk method, or solubilized in nujol. Liquids were analyzed as thin film between two NaCl blocks.

$^1$H spectra were recorded at 360 MHz on a Bruker AMX 360 spectrometer. Chemical shifts were measured relative to CDCl$_3$ (δ 7.24 ppm), CD$_3$OD (δ 3.30 ppm), acetone (d6) (δ 2.04 ppm), DMSO (d6) (δ 2.49 ppm) and expressed indirectly in relation to TMS. The following abbreviations are used to describe the signal multiplicities: s (singlet), d (doublet), t (triplet), q (quadruplet), m (multiplet). Chemical shifts are expressed in ppm and listed as follows: shift in ppm (multiplicity, integration, and coupling).

Thin-layer chromatography (TLC) was performed on plates (0.25 mm) precoated with fluorescent silica gel GF (Analtech). Reaction components were then visualized under UV light and/or with iodine and/or with a saturated solution of KMnO$_4$ in methanolic NaOH (1N).

Synthesis of 4-(R2-imino)-3-mercapto-5-(R1)-4H-1,2,4-triazoles: 3(a-j)

General Procedure:

The corresponding 4-amino-3-mercapto-5-(R1)-4H-1,2,4-triazole, 2, and aldehyde were solubilized in absolute ethanol or anhydrous THF. Typical quantities employed, were 0.50 mmol of 2, 0.75 mmol of requisite aldehyde, and 15 mL of solvent. The mixture was stirred at reflux until completion of reaction was shown by TLC ($CH_2Cl_2$/MeOH, 96/4, v/v), usually 6-60 hours, and a solid had precipitated out of solution. The flask was cooled to room temperature and stored at 0° C. overnight. The precipitate was filtered and rinsed with cold ethanol to give the expected 4-(R2-imino)-3-mercapto-5-(R1)-4H-1,2,4-triazoles, 3a-j in yields of 50-90%. The structures and the purities of products were confirmed by combustion analyses. NMRs, HRMS (Table 2) and melting points (Table 1). The specific syntheses described below are presented as representative examples.

4-[Imino-(3-(-2-nitrophenyl)-2-ethylenyl)]-3-mercapto-5-(2-thienyl)-4H-1,2,4-triazole, 3a The title compound was prepared according to the general procedure using 4-amino-3-mercapto-5-(2-thienyl)-4H-1,2,4-triazole, 2 (R1=2-thienyl), (0.10 g, 0.5 mmol), trans-2-nitrocinnamaldehyde (0.27 g, 1.5 mmol) and 4 mL of absolute ethanol at reflux for 10 hours. After filtration, a yellow solid was isolated to give 0.156 g (0.44 mmol, 87%) of 3a. $^1$H NMR (DMSO-d6): 7.21 (t, 1H, J=3.9 Hz); 7.31 (dd, 1H, J=9.0 Hz and J=16.0 Hz); 7.68 (t, 1H, J=7.9 Hz); 7.74-7.85 (m, 5H); 8.09 (dd, 2H, J=7.9 Hz and J=18.0 Hz); 9.76 (d, 1H, J=9.0 Hz). IR (nujol): 1457 $cm^{-1}$, m.p.=214°-215° C. Anal. Calcd. for $C_{15}H_{11}N_5O_2S_2$; C, 50.41; H, 3.10; N, 19.60. Found: C, 50.50; H, 2.77; N, 19.29.

4-[imino-(5-nitro-2-thienyl)]-3-mercapto-5-(4-hydroxyphenyl)-4H-1,2,4-triazole, 3b A mixture of 0.52 mmol of 2 (R1=4-hydroxyphenyl), 0.78 mmols of 5-nitro-2-thiophene carboxaldehyde, 40 mg of molecular sieves, and 18 mL of ethanol was refluxed for 72 hours, filtered hot, evaporated to about 5 mL, and chilled. The product 3b was obtained by filtration and recrystallization (methanol) in 51%, yield, m.p.=275-276° C. Exact mass (ESI) calculated for $C_{13}H_{10}N_5O_3S_2$ [M+H]=348.0220. found 348.0214.

4-[imino-(3-(5-nitro-2-furyl)-2-ethylenyl)]-3-mercapto-5-(2-furoyl)-4H-1,2,4-triazole, 3c The title compound was prepared according to the above procedure using 4-amino-3-mercapto-5-(2-furoyl)-4H-1,2,4-triazole (0.234 g, 1.28 mmol), 5-nitro-2-furanacrolein (0.322 g, 1.92 mmol) and 10 mL of anhydrous THF. After 6 hours of reflux the reaction mixture was evaporated to dryness and the orange solid was recrystallized in acetone to give 0.184 g (0.56 mmol, 44%) of 3e. $^1$H NMR ($d_6$-acetone); 6.69 (m, 1H); 7.19 (d, 1H, J=3.8 Hz); 7.26-7.46 (m, 3H); 7.62 (d, 1H, J=8.6 Hz); 7.82 (d, 1H, J=1.5 Hz); 10.23 (d, 1H, J=10.2 Hz). IR (KBr): 1369 $cm^{-1}$, m.p.=217°-218° C. Exact mass (ESI) calculated for $C_{13}H_{10}N_5O_4S$ [M+H]=332.0448. found 332.0457.

4-[imino-(5-nitro-2-furyl)]-3-mercapto-5-(2-thienyl)-4H-1,2,4-triazole, 3d

The title compound was prepared according to the above procedure using 4-amino-3-mercapto-5-(2-thienyl)-4H-1,2,4-triazole (0.196 g, 1.00 mmol), 5-nitro-2-furaldehyde (0.278 g, 1.97 mmol) and 6 mL of anhydrous THF. The reaction mixture was dry evaporated and the yellow solid was purified by a column chromatography on silica ($CHCl_3$) and then recrystallized in $CHCl_3$/Hexanes to give 72 mg (0.224 mmol, 23%) of 3d. $^1$H NMR (Acetone-d6): 7.24 (m, 1H); 7.62 (d, 1H, J=3.8 Hz); 7.71 (d, 1H, J=3.9 Hz); 7.79 (d, 1H, J=5.0 Hz); 8.00 (d, 1H, J=4.0 Hz); 10.83 (s, 1H). IR (KBr): 1363 $cm^{-1}$ m.p.=190°-191° C. Anal. Calcd. for $C_{11}H_7N_5O_3S_2$; C, 41.12; H, 2.19; N, 21.79. Found: C, 41.00; H, 2.34; N, 21.48. Exact mass (ESI) calculated for $C_{11}H_8N_5O_3S_2$ [M+H]=322.0090. found 322.0063.

4-[imino-(5-nitro-2-thienyl)]-3-mercapto-5-(2-furoyl)-4H-1,2,4-triazole, 3e

The title compound was prepared according to the above procedure using 4-amino-3-mercapto-5-(2-furoyl)-4H-1,2,4-triazole (0.2 g, 1.09 mmol), 5-nitro-2-thiophenecarboxaldehyde (0.256 g, 1.63 mmol) and 8 mL of anhydrous THF. The reaction mixture was dry evaporated and the orange solid was recrystallized in acetone to give 80 mg (0.25 mmol, 22%) of 3e. $^1$H NMR (Acetone-d6): 6.70-6.80 (m, 1H); 7.28 (d, 1H, J=3.7 Hz): 7.80-7.95 (m, 2H); 8.14 (d, 1H, J=4.2 Hz); 10.84 (s, 1H). IR (KBr): 1365 $cm^{-1}$. m.p.=244°-245° C. Anal. Calcd, for $C_{11}H_7N_5O_3S_2$: C, 41.12; H, 2.19: N, 21.79. Found: C, 40.79; H, 2.06; N, 21.58. Exact mass (ESI) calculated for $C_{11}H_8N_5O_3S_2$ [M+H]=322.0063. found 322.0064.

Synthesis of 4-(R2-imino)-3-thiomethyl-5-(R1)-4H-1,2,4-triazoles: 4(a-j)

General Procedure:

The corresponding 4-(R2-imino)-3-mercapto-5-(R1)-4H-1,2,4-triazole, 3, prepared as described above, was dissolved in anhydrous acetone containing suspended potassium carbonate. Representative quantities are 0.04 mmol of mercaptotriazole, 0.12 mmol of potassium carbonate, and 6 mL of acetone. Methyl iodide (0.12 mmol) in 2 mL of acetone was added and the reaction mixture, protected from light, was magnetically stirred for 5 hours at room temperature, filtered to remove the carbonate, evaporated to virtual dryness, dissolved in 96:4 methylenechloride:methanol, and flash filtered down a four inch column of flash-grade silica gel.

The methylenechloride:methanol mixture was used as the eluant. Yields of 75-95% of crystalline solid products, 4a-j, were obtained. Melting-points of products, once recrystalized from methanol, are shown on Table 1. Combustion analyses for C, H, and N were within 0.4% of theoretical for each molecule and two class-wide characteristic $^1$H-NMR resonances (in $d_6$-acetone) were evident in all members of class 4. These peaks appear at: 2.6±0.3 ppm (singlet) for the —$SCH_3$ and 8.5±0.3 ppm (singlet) for the H on the imine carbon or N—N=CH—.

Antibacterial Activity

The assay for antimicrobial activity is based on the determination of the minimal inhibitory concentration (MIC), a standard test for antimicrobials based on the lowest concentration that will inhibit visible growth of microorganisms. Compounds were tested using *E. coli, G. vaginalis* or *S. aureus*. Bacteria were grown on appropriate media containing a range of concentrations of the test compounds which were obtained by serial two-fold dilutions. Concentrations used were at least twice the MIC to at least ½ the break point for susceptibility to inhibition. MICs were determined spectrophotometrically by measuring changes in absorbance of bacterial cultures in the absence and presence of the test compounds.

Anti-Inflammatory Activity

The assay for measurement of anti-inflammatory activity is based on the ability of the cytokine gamma interferon to induce the formation of nitric oxide synthase and subsequently of nitric oxide itself in keratinocytes. The method reported by Laskin, et al. was followed (Heck D E; Laskin D L Gardner C R; Laskin J D, Epidermal growth Factor suppresses nitric oxide and hydrogen peroxide production by keratinocytes. *J. Biol. Chem.*, 1992, 30, 21277; and DeGeorge G L, Heck D E, Laskin J D, Arginine metabolism in keratinocytes and macrophages during nitric oxide biosynthesis: multiple modes of action of nitric oxide synthase inhibitors, *Biochem. Pharmacol.*, 1997 Jul. 1; 54(1):103-12; both of which are incorporated by reference). PAM 212 keratinocytes were maintained in a growth medium of Dulbecco's modified Eagles's medium (DMEM) supplemented with 10% fetal calf serum.

Figure 2:
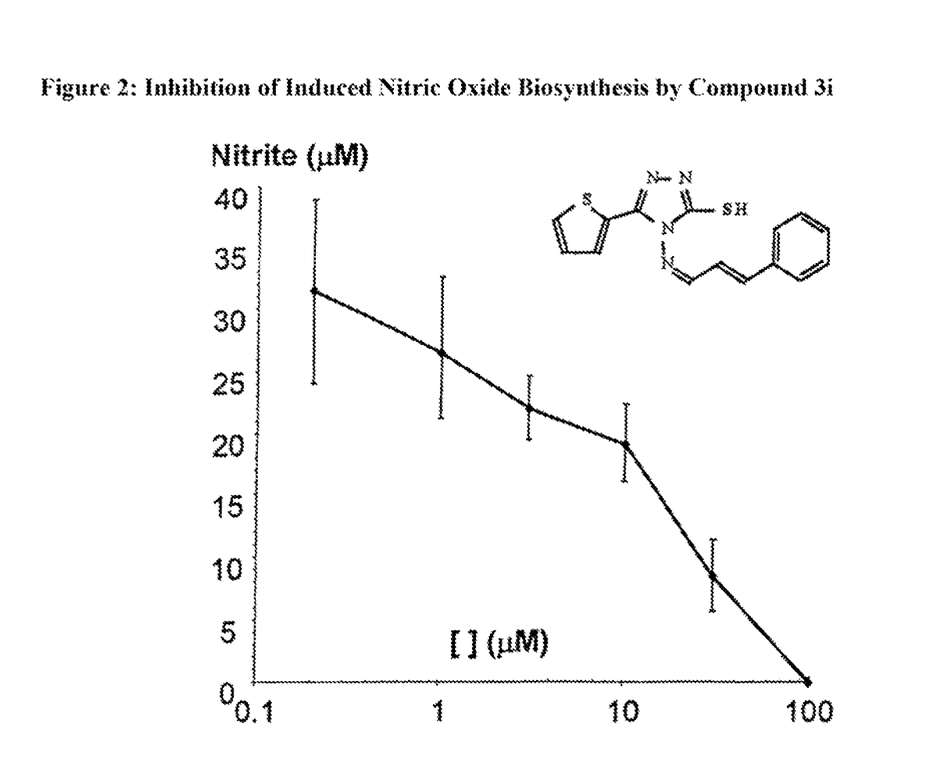
FIG. 2 shows a graph of the inhibition of induced nitric oxide biosynthesis by compound 3i, nitrite produced versus concentration of 3i.

For each assay the cells were inoculated into a 24-well tissue culture plate at 250,000 cells per well in growth medium. After 24 hours the medium was changed to phenol red and serum-free DMEM containing 100 U/ml of gamma interferon. Nitric oxide production was thereby initiated and at 72 hours post inoculation was quantified spectrophotometrically by measuring the accumulation of nitrite in the culture medium using the Greiss reagent. This was done by drawing an aliquot of the culture medium and mixing it with equal volumes of 1.0% sulfanilamide and 0.1% N-1-naphthylethylene diamine in 50% phosphoric acid. After 15 minutes at ambient temperature, the absorbance was measured. at 540 nm using a microplate reader and the results were compared to a calibration curve prepared from standard solutions of sodium nitrite treated as described above. Compounds according to the present invention were assayed for their anti-inflammatory activity by examining their ability to suppress nitric oxide production in this assay. A typical response curve for inhibitors of nitric oxide synthase is shown for 3i in FIG. 2.

It is understood that the specific embodiments of the invention disclosed herein are not to be construed to limit the present invention in any way, and that other embodiments which might occur to one skilled in the art, fall within the scope of the present invention.

All references cited herein are incorporated herein by reference in their entireties.

TABLE I

Biological Activities and Physical Properties of Triazole Aldimines

| Cmpd Class | Substitution[3] R1 | R2 | Antibacterial MIC (µg/mL) E. Coli | G. Vaginalis | Nitric oxide inhibition $IC_{50}$ in µM | m.p. (° C.) |
|---|---|---|---|---|---|---|
| NF[1] | — | — | 1.2 | 11.9 | (see Note[2]) | 263 |
| 3a | 2-thienyl | 2-nitrocinnamyl | IA | IA | 14 | 214-215 |
| 4a | 2-thienyl | 2-nitrocinnamyl | IA | IA | 3.0 | 165-166 |
| 3b | 4-hydroxyphenyl | 5-nitro-2-thienyl | ND | ND | ND | 275-276 |
| 4b | 4-hydroxyphenyl | 5-nitro-2-thienyl | 18.1 | 1.8 | ND | 229-230 |
| 3c | 2-furyl | 5-nitro-2-furyl vinyl | 16.6 | 16.6 | ND | 217-218 |
| 3d | 2-thienyl | 5-nitro-2-furyl | 16.0 | 3.2 | ND | 190-191 |
| 4d | 2-thienyl | 5-nitro-2-furyl | 16.8 | 16.8 | ND | 179-180 |

TABLE I-continued

Biological Activities and Physical Properties of Triazole Aldimines

| Cmpd Class | Substitution³ R1 | R2 | Antibacterial MIC (µg/mL) E. Coli | G. Vaginalis | Nitric oxide inhibition IC₅₀ in µM | m.p. (° C.) |
|---|---|---|---|---|---|---|
| 3e | furan | thiophene-NO₂ | IA | 16.1 | 2.0 | 244-245 |
| 4e | furan | thiophene-NO₂ | 16.8 | 16.8 | ND | 170-171 |
| 3f | thiophene | thiophene-NO₂ | ND | ND | ND | 241-243 |
| 4f | thiophene | thiophene-NO₂ | 17.6 | 1.8 | ND | 189-190 |
| 3g | furan | furan-NO₂ | 15.3 | 15.3 | ND | 177-179 |
| 4g | furan | furan-NO₂ | 16.0 | 16.0 | ND | 171-172 |
| 3h | thiophene | CH₃-phenyl | ND | ND | 24 | 200-201 |
| 3i | thiophene | phenyl | ND | ND | 22 | 206-207 |
| 4i | thiophene | phenyl | ND | ND | 14 | 250-251 |
| 3j | furan | phenyl | ND | ND | 15 | 181-182 |
| 4j | furan | phenyl | ND | ND | 14 | 128-130 |

¹NF = Nitrofuratoin (structure shown below),
IA = Inactive, and
ND = Not Determined.
General structures for compound classes 3 and 4 are shown below.
Nitrofurantoin and the aldimines were tested as antibacterial agents using *E. coli* and *G. vaginalis*.
Compounds 4e and 4d were also tested as inhibitors of *S. aureus*.
The MIC's for 4e and 4d were found to be 0.39 µg/ml and 1.56 µg/ml, respectively.
²Note.
Nitrofurantoin is a pro-inflammatory not an anti-inflammatory, see references 15 and 16.
IC₅₀ = concentration of test compound inhibiting nitric oxide production induced by gamma interferon in PAM212 keratinocytes by 50%.
³Structures for Table 1:

TABLE I-continued

Biological Activities and Physical Properties of Triazole Aldimines

| Cmpd Class | Substitution[3] | | Antibacterial MIC (μg/mL) | | Nitric oxide inhibition | m.p. |
|---|---|---|---|---|---|---|
| | R1 | R2 | E. Coli | G. Vaginalis | IC$_{50}$ in μM | (° C.) |

NF: structure with O$_2$N-furan-CH=N-hydantoin

3: triazole structure with R1, SH, N=CH-R2

4: triazole structure with R1, SCH$_3$, N=CH-R2

TABLE 2

ESI High Resolution Mass Spectrometry Data.

| Compound | [M + H] formula | Calculated Mass | Found Mass |
|---|---|---|---|
| 3a | C$_{15}$H$_{12}$N$_5$O$_2$S$_2$ | 359.0505 | NA[1] |
| 4a | C$_{16}$H$_{14}$N$_5$O$_2$S$_2$ | 372.0583 | 372.0583 |
| 3b | C$_{13}$H$_{10}$N$_5$O$_3$S$_2$ | 348.0220 | 348.0214 |
| 4b | C$_{14}$H$_{12}$N$_5$O$_3$S$_2$ | 362.0376 | 362.0364 |
| 3c | C$_{13}$H$_{10}$N$_5$O$_4$S | 332.0448 | 332.0457 |
| 3d | C$_{11}$H$_8$N$_5$O$_3$S$_2$ | 322.0063 | 322.0090 |
| 4d | C$_{12}$H$_{10}$N$_5$O$_3$S$_2$ | 336.0220 | 336.0236 |
| 3e | C$_{11}$H$_8$N$_5$O$_3$S$_2$ | 322.0063 | 322.0064 |
| 4e | C$_{12}$H$_{10}$N$_5$O$_3$S$_2$ | 336.0220 | 336.0230 |
| 3f | C$_{11}$H$_8$N$_5$O$_2$S$_3$ | 337.9913 | NA |
| 4f | C$_{12}$H$_{10}$N$_5$O$_2$S$_3$ | 351.9991 | 351.9999 |
| 3g | C$_{11}$H$_8$N$_5$O$_4$S | 306.0292 | 306.0293 |
| 4g | C$_{12}$H$_{10}$N$_5$O$_4$S | 320.0448 | 320.0453 |
| 3h | C$_{16}$H$_{15}$N$_4$S$_2$ | 327.0733 | 327.0721 |
| 3i | C$_{15}$H$_{13}$N$_4$S$_2$ | 313.0576 | 313.0566 |
| 4i | C$_{16}$H$_{15}$N$_4$S$_2$ | 327.0733 | 327.0740 |
| 3j | C$_{15}$H$_{13}$N$_4$OS | 297.0805 | 297.0805 |
| 4j | C$_{16}$H$_{15}$N$_4$OS | 311.0961 | 311.0971 |

[1]NA = not available

What is claimed is:

1. A compound of Formula (4):

(structure 4: triazole with R1, SMe, N=CH-R2)

wherein
R1 is thien-2-yl and R2 is 5-nitrothien-2-yl, or
R1 is 4-hydroxyphenyl and R2 is 5-nitrothien-2-yl.

2. A pharmaceutical composition comprising at least one compound of claim 1 and at least one compound selected from the group of pharmaceutically acceptable adjuvants, carriers, diluents and excipients.

3. A topical pharmaceutical composition comprising the composition of claim 2, wherein said at least one compound selected from the group of pharmaceutically acceptable adjuvants, carriers, diluents and excipients is adapted for topical application.

* * * * *